(12) United States Patent
Butler et al.

(10) Patent No.: US 8,715,321 B2
(45) Date of Patent: May 6, 2014

(54) SPINAL FACET FASTENER

(75) Inventors: Michael S. Butler, St. Charles, IL (US); Brian D. Hartsell, Aurora, IL (US)

(73) Assignee: Life Spine, Inc., Hoffman Estates, IL (US)

( * ) Notice: Subject to any disclaimer, the term of this patent is extended or adjusted under 35 U.S.C. 154(b) by 564 days.

(21) Appl. No.: 12/572,101

(22) Filed: Oct. 1, 2009

(65) Prior Publication Data
US 2010/0082065 A1 Apr. 1, 2010

Related U.S. Application Data (60) Provisional application No. 61/101,800, filed on Oct. 1, 2008.

(51) Int. Cl.
A61B 17/70 (2006.01)
(52) U.S. Cl.
USPC .......................................................... 606/247
(58) Field of Classification Search
USPC ..................... 606/246–249, 74–75, 219–220; 623/17.11–17.16
See application file for complete search history.

(56) References Cited

U.S. PATENT DOCUMENTS

| | | | | |
|---|---|---|---|---|
| 4,500,239 A * | 2/1985 | Liebig | ........................ | 411/65 |
| 5,089,009 A * | 2/1992 | Green | ........................ | 606/219 |
| 5,139,379 A * | 8/1992 | Hasan et al. | ........................ | 411/368 |
| 5,352,229 A * | 10/1994 | Goble et al. | ........................ | 606/75 |
| 5,472,452 A * | 12/1995 | Trott | ........................ | 606/232 |
| D374,482 S * | 10/1996 | Goble et al. | ........................ | D24/145 |
| 5,643,321 A * | 7/1997 | McDevitt | ........................ | 606/232 |
| 5,785,713 A * | 7/1998 | Jobe | ........................ | 606/75 |
| 5,899,904 A * | 5/1999 | Errico et al. | ........................ | 606/256 |
| 6,056,751 A * | 5/2000 | Fenton, Jr. | ........................ | 606/28 |
| 6,251,143 B1 * | 6/2001 | Schwartz et al. | ........................ | 623/23.72 |
| 6,524,316 B1 * | 2/2003 | Nicholson et al. | ........................ | 606/326 |
| 6,648,893 B2 * | 11/2003 | Dudasik | ........................ | 606/327 |
| 6,835,206 B2 * | 12/2004 | Jackson | ........................ | 623/17.11 |
| 7,371,238 B2 * | 5/2008 | Soboleski et al. | ........................ | 606/246 |
| 7,481,832 B1 * | 1/2009 | Meridew et al. | ........................ | 606/319 |
| 7,585,307 B2 * | 9/2009 | Fontayne et al. | ........................ | 606/153 |
| 7,935,136 B2 * | 5/2011 | Alamin et al. | ........................ | 606/279 |
| 8,070,782 B2 * | 12/2011 | McKay | ........................ | 606/279 |
| 8,241,308 B2 * | 8/2012 | Kortenbach et al. | ........................ | 606/151 |
| 8,267,966 B2 * | 9/2012 | McCormack et al. | ........................ | 606/247 |
| 8,317,839 B2 * | 11/2012 | Pavlov et al. | ........................ | 606/279 |
| 8,419,780 B2 * | 4/2013 | Bickley et al. | ........................ | 606/326 |
| 8,425,558 B2 * | 4/2013 | McCormack et al. | ........................ | 606/247 |
| 2002/0007182 A1 * | 1/2002 | Kim | ........................ | 606/53 |
| 2002/0095155 A1 * | 7/2002 | Michelson | ........................ | 606/61 |
| 2002/0099378 A1 * | 7/2002 | Michelson | ........................ | 606/61 |
| 2004/0127989 A1 * | 7/2004 | Dooris et al. | ........................ | 623/13.17 |

(Continued)

*Primary Examiner* — Ellen C Hammond
*Assistant Examiner* — Jacqueline Johanas
(74) *Attorney, Agent, or Firm* — Foley & Lardner LLP (57) ABSTRACT

A spinal implant includes a first leg configured to abut a surface of an inferior articular process of a first vertebra that forms one portion of a spinal facet joint between the first vertebra and an adjacent second vertebra, a second leg configured to abut a surface of a superior articular process of the adjacent second vertebrae that forms another portion of the spinal facet joint between the first vertebra and the adjacent second vertebra, and a cross-member connected between the first and second legs and maintaining the first and second legs in a spaced-apart relationship. The spinal implant may restrict flexion and/or extension of the spinal facet joint when received about the spinal facet joint.

16 Claims, 9 Drawing Sheets

(56) References Cited

U.S. PATENT DOCUMENTS

| | | |
|---|---|---|
| 2004/0220574 A1* | 11/2004 | Pelo et al. .................. 606/73 |
| 2005/0267480 A1* | 12/2005 | Suddaby .................... 606/75 |
| 2006/0004367 A1* | 1/2006 | Alamin et al. .............. 606/74 |
| 2006/0058802 A1* | 3/2006 | Kofoed ...................... 606/75 |
| 2006/0190081 A1 | 8/2006 | Kraus et al. |
| 2006/0235387 A1 | 10/2006 | Peterman |
| 2006/0247632 A1* | 11/2006 | Winslow et al. ............ 606/61 |
| 2007/0016196 A1* | 1/2007 | Winslow et al. ............ 606/61 |
| 2007/0055252 A1 | 3/2007 | Blain et al. |
| 2007/0162030 A1* | 7/2007 | Aranyi et al. .............. 606/75 |
| 2007/0191850 A1* | 8/2007 | Kim et al. .................. 606/75 |
| 2007/0244483 A9* | 10/2007 | Winslow et al. ............ 606/61 |
| 2007/0250166 A1* | 10/2007 | McKay ...................... 623/17.11 |
| 2008/0077144 A1* | 3/2008 | Crofford .................... 606/75 |
| 2008/0221621 A1* | 9/2008 | Snyder et al. .............. 606/263 |
| 2008/0221692 A1* | 9/2008 | Zucherman et al. ....... 623/17.16 |
| 2008/0255666 A1* | 10/2008 | Fisher et al. .............. 623/17.16 |
| 2008/0319550 A1* | 12/2008 | Altarac et al. ............ 623/17.16 |
| 2009/0163920 A1* | 6/2009 | Hochschuler et al. ........ 606/74 |
| 2009/0187219 A1* | 7/2009 | Pachtman et al. ........... 606/324 |
| 2009/0224023 A1* | 9/2009 | Moskowitz et al. ....... 227/181.1 |
| 2010/0036496 A1* | 2/2010 | Yu et al. .................... 623/17.14 |
| 2010/0069912 A1* | 3/2010 | McCormack et al. ........ 606/90 |
| 2010/0076490 A1* | 3/2010 | Greenwald et al. .......... 606/279 |
| 2010/0106250 A1* | 4/2010 | Abdou ...................... 623/17.11 |
| 2010/0137989 A1* | 6/2010 | Armstrong et al. ........ 623/17.16 |
| 2010/0241164 A1* | 9/2010 | Fischer et al. .............. 606/247 |
| 2011/0004247 A1* | 1/2011 | Lechmann et al. .......... 606/247 |
| 2011/0077685 A1* | 3/2011 | Carls et al. .................. 606/247 |
| 2013/0012994 A1* | 1/2013 | McCormack et al. ........ 606/247 |

\* cited by examiner

SPINAL FACET FASTENER

RELATED APPLICATIONS

This patent application claims the benefit of and/or priority to U.S. Provisional Patent Application Ser. No. 61/101,800 filed Oct. 1, 2008, entitled "Spinal Facet Fastener" the entire contents of which is specifically incorporated herein by this reference.

BACKGROUND OF THE INVENTION

1. Field of the Invention

The present invention relates to devices for the spine and, more particularly, to devices for restricting, limiting and/or stopping motion between adjacent vertebrae.

2. Background Information

As we age various changes can occur in the body especially with respect to the spinal column or spine. For instance, the ligaments of the spine can thicken and calcify (i.e. harden from deposits of calcium), bone and joints may enlarge, bone spurs called osteophytes may form, spinal discs may break down, collapse, bulge and/or herniate. Moreover, one vertebra may slip over another vertebra (spondylolisthesis). Facet joints of the spine can also be affected. The facet joints are found at every spinal level (except at the top level) and provide about 20% of the torsional (twisting) stability in the neck and lower back.

Facet joints are hinge-like and link vertebrae together. They are located at the back or posterior of the spine. Each vertebra has two sets or pairs of facet joint portions that join with two sets or pairs of facet joint portions of adjacent vertebrae. Particularly each vertebra has a pair of upward facing facet joint portions (the superior articular facets) and a pair of downward facing facet joint portions (the inferior articular facets). The pair of superior articular facets of one vertebra is linked to a pair of inferior articular facets of a superiorly adjacent (upper) vertebra, while the pair of inferior articular facets of the one vertebra is linked to a pair of superior articular facets of an inferiorly adjacent (lower) vertebra. Thus, each vertebra is linked to an upper adjacent vertebra by two facet joints and to a lower adjacent vertebra by two facet joints.

The facet joints are synovial joints meaning that each joint is surrounded by a capsule of connective tissue and produces a fluid to nourish and lubricate the facet joint. The facet joints slide or glide smoothly (articulate) on each other and therefore both sliding surfaces are coated by a very low friction, most cartilage. A small sack or capsule surrounds each facet joint and provides a sticky lubricant for the joint. Each sack has a rich supply of tiny nerve fibers that provide a warning when irritated. The facet joints allow flexion (bend forward), extension (bend backward), and twisting motion, while restricting certain types of movement. The spine is made stable due to the interlocking nature of adjacent vertebrae through the facet joints. Each facet joint is positioned at each level to provide the needed limits to motion, especially to rotation and to prevent forward slipping (spondylolisthesis) of that vertebra over the one below.

Facet joints are in almost constant motion with the spine and quite commonly simply wear out or become degenerated in many people. When facet joints become worn or torn the cartilage may become thin or disappear and there may be a reaction of the bone of the joint underneath producing overgrowth of bone spurs and an enlargement of the joints. The joint is then said to have arthritic (literally, joint inflammation-degeneration) changes, or osteoarthritis that can produce considerable back pain on motion. This condition may also be referred to as "facet joint disease" or "facet joint syndrome".

Moreover, facet joints become especially vulnerable when the intervertebral disc is injured. This is true because as the disc degenerates, the volume of the disc is reduced and the disc space tends to flatten out. The disc therefore loses height and the space between the vertebral bodies becomes narrowed. The flattening disc space provides much less support for the facet joints at that particular level, and the joints become subject to increased stress. Facet joint pain is often felt in the spinal area rather than in an arm or leg.

It is therefore sometimes desirable to restrict, limit or immobilize a spinal facet joint because of disease, injury, trauma or the like.

In view of the above it would thus be desirable to have a spinal device for restricting, limiting and/or immobilizing a spinal facet joint.

SUMMARY OF THE INVENTION

The present invention is a spinal implant configured to hold, restrict and/or limit flexion and/or extension of a spinal facet joint and/or immobilize movement thereof. The present spinal implant is formed as a spinal facet fastener having segments configured for reception in, on and/or about vertebral bone of a spinal facet joint. The spinal facet fastener may be formed as a clamp, staple, tack, retainer or the like. The spinal facet fastener is formed of a biocompatible material such as PEEK (polyetheretherketone) but may be formed of other biocompatible materials such as a biocompatible metal (e.g. titanium or stainless steel).

In one form, the present spinal facet fastener has surfaces that are configured to abut vertebral bone surfaces of a spinal facet joint to hold, restrict and/or limit flexion and/or extension of the spinal facet joint and/or immobilize movement thereof. In another form, the present spinal facet fastener has members that are configured for reception in vertebral bone of the vertebral bone portions that form the spinal facet joint. In this form, the spinal facet fastener may include an anchoring element that is configured for reception between the vertebral bone portions that form the spinal facet joint.

In the first form identified above, the spinal facet fastener is formed generally as a U-shaped member or body having a first leg and a second leg extending from and separated a distance by a cross member. The U-shaped body thereby defines an inner area for receipt of a spinal facet joint that is bounded by the first leg, the second leg and the cross member. The first leg is configured to abut a surface of an inferior articular process of a first vertebra while the second leg is configured to abut a surface of a superior articular process of a second vertebra that is adjacent the first vertebra. Particularly, an inner surface of the first leg contacts and/or abuts the portion of the inferior articular process that forms one portion of the spinal facet joint of one of the adjacent vertebrae while an inner surface of the second leg contacts and/or abuts the portion of the superior articular process that forms another portion of the spinal facet joint of the other of the adjacent vertebrae. In this form, the present spinal facet fastener may be considered a spinal facet clamp.

In one form of the present spinal facet clamp, the inner or inside surface of the first leg and the inner or inside surface of the second leg each are generally flat, planar or smooth. The inner or inside surface of the cross member is also generally flat, planar or smooth.

In another form of the present spinal facet clamp, the inner or inside surface of the first leg and the inner or inside surface of the second leg each has a plurality of teeth or serrations.

Each plurality of teeth preferably, but not necessarily, extends along the longitudinal length of the inner surface from an end of the respective leg to proximate the cross member.

The spinal facet clamp may be formed with a fixed width or may be formed with as adjustable in width.

In the second form identified above, the spinal facet fastener is formed generally as a U-shaped member or body having a first leg and a second leg extending from and separated a distance by a cross member. A shaft in the form of a spike extends from the cross-member between the first and second legs. The first leg is configured to be received in an inferior articular process of a first vertebra while the second leg is configured to be received in a superior articular process of a second vertebra that is adjacent the first vertebra. In this form, the present spinal facet fastener may be considered a spinal facet staple or tack. The first and second legs may be smooth or have serrations as described above. Likewise, the center shaft may be smooth or have serrations thereabout.

The second form of the present spinal facet fastener may be used with a spinal facet joint anchoring element that is configured for receipt in the spinal facet joint. The spinal facet joint anchoring element pivotally receives the shaft of the spinal facet fastener while the first and second legs thereof extend over the respective adjacent bony structures.

In one form of the spinal facet joint anchoring element, tabs thereof are configured to interact with the shaft of the tack to expand outward once the tack has been inserted into and about the spinal facet joint. This effectively wedges the anchoring element in place, further preventing back-out and/or facet movement.

BRIEF DESCRIPTION OF THE DRAWINGS

The above mentioned and other features, advantages and objects of this invention, and the manner of attaining them, will become apparent and the invention itself will be better understood by reference to the following description of embodiments of the invention taken in conjunction with the accompanying drawings, wherein.

Like reference numerals indicate the same or similar parts throughout the several figures.

A discussion of the features, functions and/or configurations of the components depicted in the various figures will now be presented. It should be appreciated that not all of the features of the components of the figures are necessarily described. Some of these non discussed features as well as discussed features are inherent from the figures. Other non discussed features may be inherent in component geometry and/or configuration.

DETAILED DESCRIPTION OF THE INVENTION

Referring to the figures, there is depicted various spinal facet fasteners fashioned in accordance with the present principles. The spinal facet fastener may be considered a clamp, tack, staple, retainer or holder depending on its form (hereinafter, collectively, spinal facet fastener). All of the spinal facet fasteners are fashioned from a biocompatible material such as plastic (e.g. polyetheretherketone (PEEK)), metal (e.g. titanium, stainless steel or alloy), a polymer, a composite, or the like.

Figure 1:
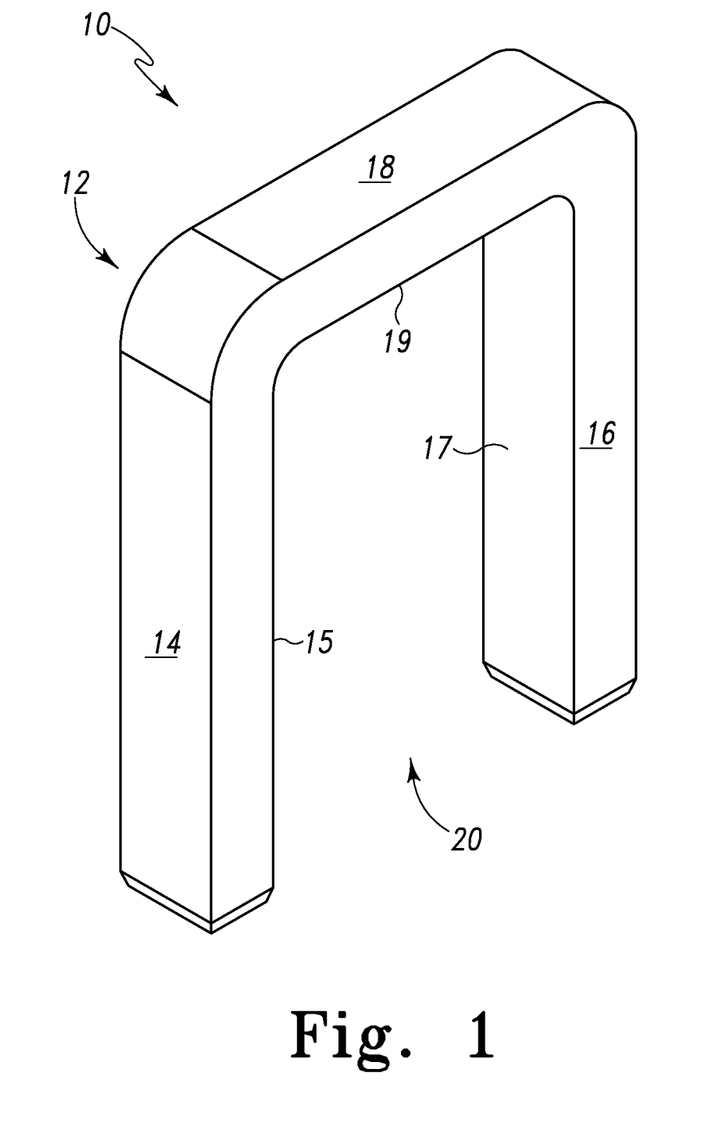
FIG. 1 is an enlarged isometric view of an embodiment of a spinal facet fastener fashioned in accordance with the principles of the present invention.

Referring particularly to FIG. 1, there is depicted a spinal facet fastener fashioned as a spinal facet clamp, generally designated 10. The spinal facet clamp 10 is characterized by a preferably, but not necessarily, unitary body 12. The body 12 has a first leg, member, post or the like 14 (collectively, leg 14), a second leg, member, post or the like 16 (collectively, leg 16) and a cross member 18 that all form a generally U-shaped body. It should be appreciated that the terms first and second are arbitrary unless indicated otherwise.

The first and second legs 14, 16 extend in the same direction from opposite ends of the cross-member 18. Preferably, but not necessarily, the first and second legs 14, 16 are at least generally parallel with one another, but may be skewed relative to one another if desired. The body 12 defines an area 20 that is bounded on three sides by the first leg 14, the second leg 16 and the cross member 18. Particularly, the open area 20 is bounded by an inner (or inner facing) surface 15 of the first leg 14, an inner (or inner facing) surface 17 of the second leg 16, and an inner (or inner facing) surface 19 of the cross member 18. The inner surfaces 15, 17 and 19 of the first and second legs 14, 16 and the cross member 18 of the spinal facet clamp 10 are generally flat, smooth or planar.

Figure 2:
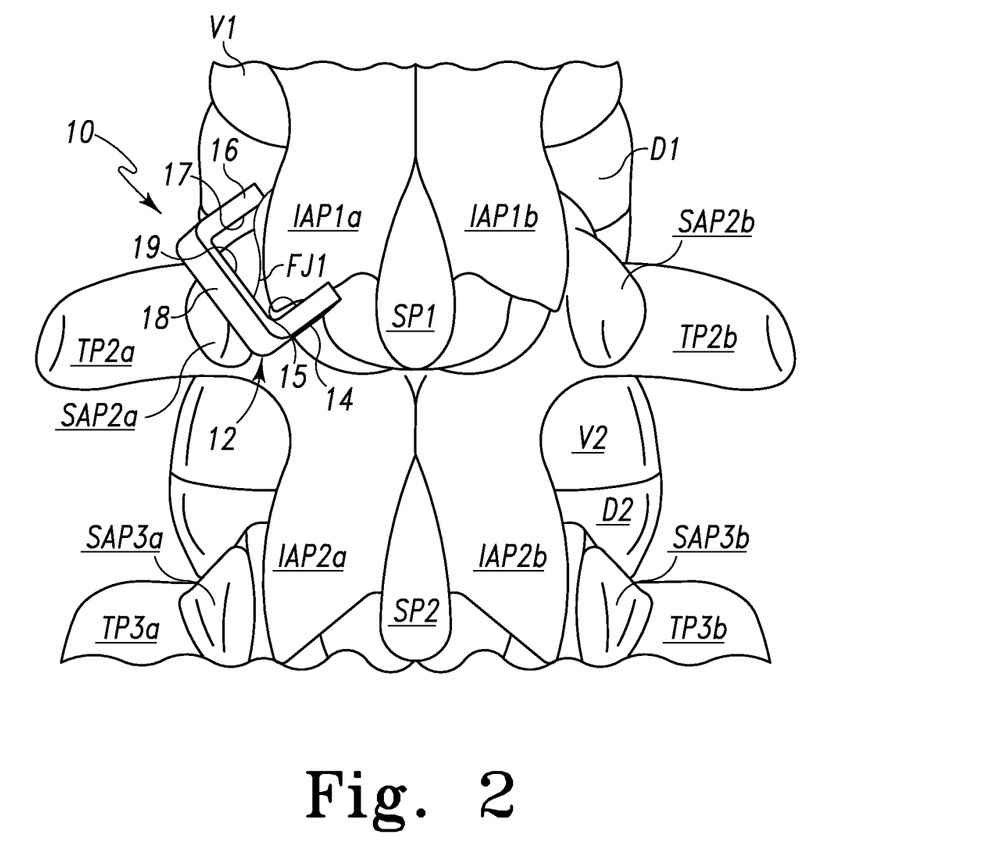
FIG. 2 is a posterior view of a portion of a human spine with the spinal facet fastener of FIG. 1 situated thereon.
Figure 3:
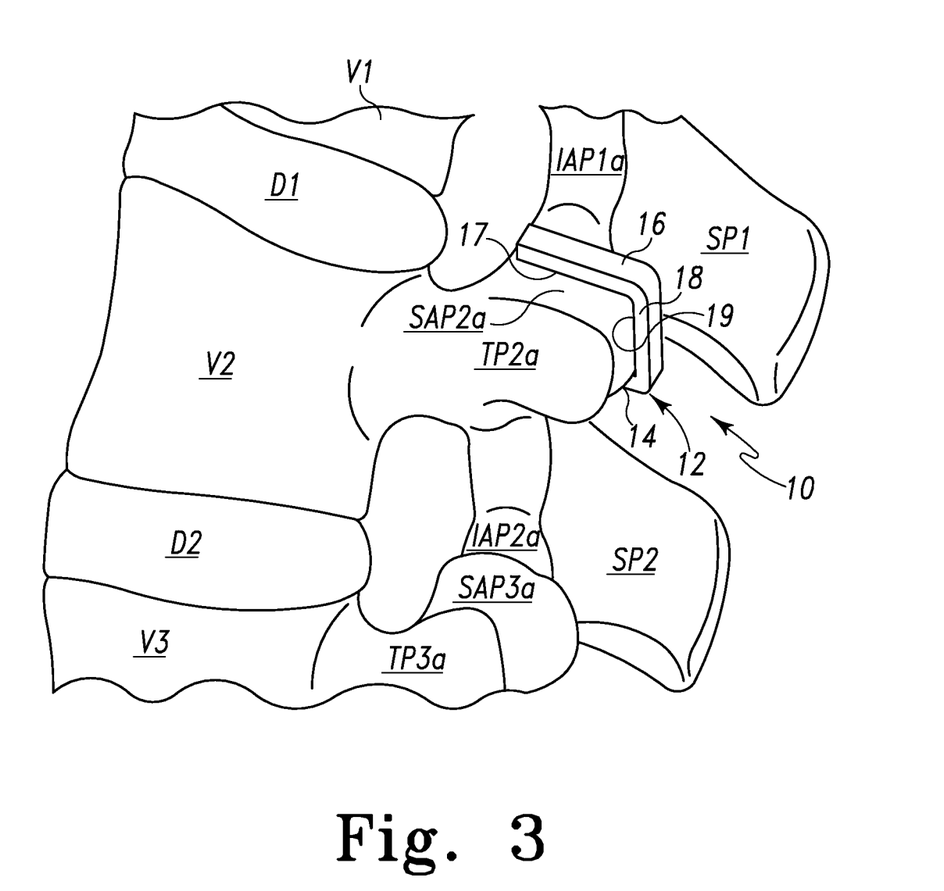
FIG. 3 is a lateral view of the portion of the human spine of FIG. 2 showing the spinal facet fastener of FIG. 1.

The inner surfaces 15, 17 are designed to abut or wedge against a spinal facet joint—i.e. a surface of an inferior articular process of one vertebra and a surface of a superior articular process of another vertebra (such as is shown in FIGS. 2 and 3 wherein the spinal facet clamp 10 is situated on the spinal facet joint FJ1 and particularly about one inferior articular process of a first vertebra V1 (labeled "IAP1*a*") of the spinal facet joint FJ1, and about one superior articular process of a second vertebra V2 (labeled "SAP2*a*") of the spinal facet joint FJ1). The spinal facet clamp 10 holds, restrains and/or retains the spinal facet joint FJ1. The spinal facet clamp 10 can thereby limit articulation of the spinal facet joint FJ1 or immobilize articulation of the spinal facet joint FJ1.

A portion of a spinal column or spine is shown in FIGS. 2 and 3 representing any portion of the spine in which the present invention may be used such as the lumbar or thoracic portions. Particularly, three (3) vertebrae are shown in FIGS. 2 and 3 illustrating the use of the spinal facet device 10 relative to two of the three vertebrae, the three vertebrae labeled V1, V2 and V3. Disc D1 separates vertebrae V1 and V2 while disc D2 separates vertebrae V2 and V3. The respective parts of these vertebrae are labeled with its respective number while transverse processes are labeled beginning with the letters "TP", the superior articular processes are labeled beginning with the letters "SAP", the inferior articular processes are labeled beginning with the letters "IAP", while the spinous processes are labeled beginning with the letters "SP." As best seen in FIG. 3, the spine depicted therein is in a natural upright (not extended or flexed) position with the spinal facet clamp 10 situated thereon. The present spinal facet clamp exerts pressure against the facet joint FJ1. Depending on the amount of pressure exerted by the legs of the present spinal facet clamp against the facet joint FJ1, the spinal facet clamp 10 either just holds the facet joint together while allowing at least some articulation or restrains the facet joint FJ1 from any articulation (immobilization of the facet joint).

It should be appreciated that while only one spinal facet clamp is being used on the portion of a spine that is depicted in FIGS. 2 and 3, two or more facets clamps may be used as appropriate. Facet clamps may be used in pairs for upper or lower facet joint pair use. Alternatively or additionally, two or more facet clamps may be positioned axially along the vertebrae.

Figure 4:
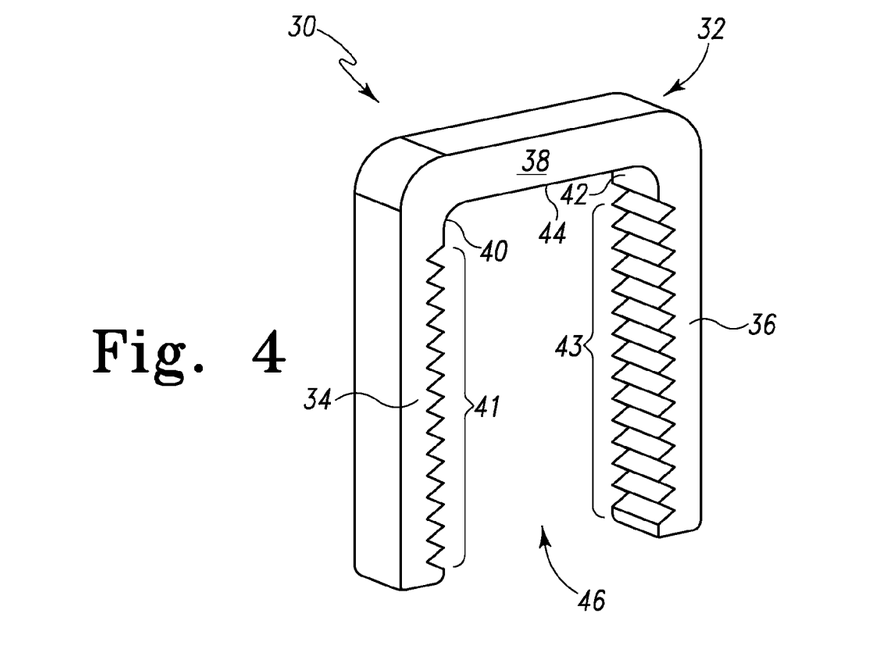
FIG. 4 is an enlarged isometric view of another embodiment of a spinal facet fastener fashioned in accordance with the principles of the present invention.

Referring to FIG. 4, there is depicted an alternate embodiment of the present spinal fact clamp, generally designated 30. The spinal facet clamp 30 is likewise fashioned from a biocompatible material such as plastic (e.g. polyetheretherketone (PEEK)), metal (e.g. titanium, stainless steel or alloy), a polymer, a composite, or the like and is characterized by a preferably, but not necessarily, unitary body 32. The body 32 has a first leg, member, post or the like 34, a second leg, member, post or the like 36 and a cross-member 38 that all generally form a U-shaped body. It should be appreciated that the terms first and second are arbitrary unless indicated otherwise.

The first and second legs 34, 36 extend in the same direction from opposite ends of the cross-member 38. Preferably, but not necessarily, the first and second legs 34, 36 are at least generally parallel with one another, but may be skewed relative to one another if desired. The body 32 defines an area 46 that is bounded on three sides by the first leg 34, the second leg 36 and the cross member 38. Particularly, the open area 46 is bounded by an inner (or inner facing) surface 40 of the first leg 34, an inner (or inner facing) surface 42 of the second leg 36, and an inner (or inner facing) surface 44 of the cross member 18.

The inner surface 40 of the first leg 34 has a plurality of teeth, grooves or serrations 41 that preferably, but not necessarily, extend a length proximate an end of the first leg 34 to proximate the inner surface 44 of the cross member 38. The length of teeth may be less than shown. As well, the number of teeth and their configuration may be different than that shown. Alternatively, the teeth 41 may be grouped with planar regions therebetween. Various configurations are contemplated. The inner surface 42 of the second leg 36 likewise has a plurality of teeth, grooves or serrations 43 that preferably, but not necessarily, extend a length proximate an end of the second leg 36 to proximate the inner surface 44 of the cross member 38. The length of teeth may be less than shown. As well, the number of teeth and their configuration may be different than that shown. Alternatively, the teeth 43 may be grouped with planar regions therebetween. Various configurations are contemplated.

In all cases, the inner teeth 41, 43 are designed to abut or wedge against a spinal facet joint as described above and to provide anti-back-out and one way installation features. It should be appreciated that the spinal facet clamp 30 may be used instead of or in conjunction with the spinal facet clamp 10 as desired and/or is appropriate. Therefore, the depiction and description regarding the spinal facet clamp 10 of FIGS. 2 and 3 is applicable to the spinal facet clamp 30 and all other facet clamps encompassed within the present invention. Thus, the spinal facet clamp 30 is thus configured to hold, restrain and/or retain a spinal facet joint. The spinal facet clamp 30 can thereby limit articulation of the spinal facet joint FJ1 or immobilize articulation of the spinal facet joint FJ1.

The spinal facet clamps 10 and 30 have a fixed width. As such, the spinal facet clamps 10 and 30 are made having various widths. The spinal facet clamp 50 of FIG. 5 (discussed below) however, has an adjustable width.

Figure 5:
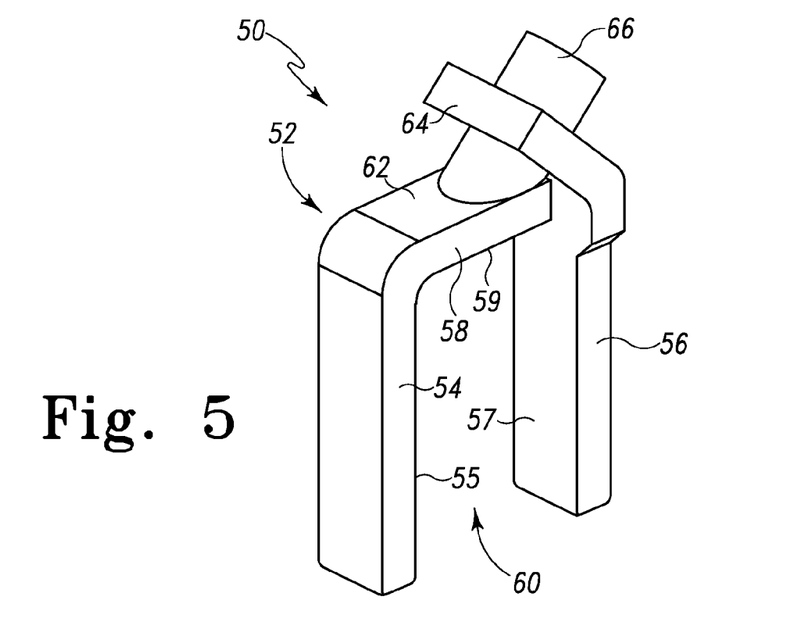
FIG. 5 is an enlarged isometric view of another embodiment of a spinal fact fastener fashioned in accordance with the principles of the present invention.

Referring to FIG. 5, there is depicted an alternate embodiment of the present spinal fact clamp, generally designated 50. The adjustable width spinal facet clamp 50 is likewise fashioned from a biocompatible material such as plastic (e.g. polyetheretherketone (PEEK)), metal (e.g. titanium, stainless steel or alloy), a polymer, a composite, or the like and is characterized by a preferably, but not necessarily, unitary body 62. The body 62 has a first leg, member, post or the like 54, a second leg, member, post or the like 56 and a cross-member 58 that all generally form a U-shaped body. It should be appreciated that the terms first and second are arbitrary unless indicated otherwise.

The first and second legs 54, 56 extend in the same direction from opposite ends of the cross-member 58. Preferably, but not necessarily, the first and second legs 54, 56 are at least generally parallel with one another, but may be skewed relative to one another if desired. The body 52 defines an area 60 that is bounded on three sides by the first leg 54, the second leg 56 and the cross member 58. Particularly, the open area 60 is bounded by an inner (or inner facing) surface 55 of the first leg 54, an inner (or inner facing) surface 57 of the second leg 56, and an inner (or inner facing) surface 59 of the cross member 58. The inner surfaces 55, 57 and 59 of the first and second legs 54, 56 and the cross member 58 of the spinal facet clamp 10 are generally flat, smooth or planar.

The body 52 further includes a yoke 64 that extends from the top of the second leg 56 with a rod 66 extending therethrough. A nut (not shown) or other type of adjustment device is provided on the rod 66 in order to tighten the spinal facet clamp 50. This allows the spinal facet clamp 50 to provide more clamping force on the spinal facet joint as desired. While not shown, the spinal facet clamp 50 may include serrations on the inner surfaces 55, 57 of first and second legs 54, 56 in like manner as the spinal facet clamp 30. This provides anti-kick-out and back-out provisions.

Figure 6:
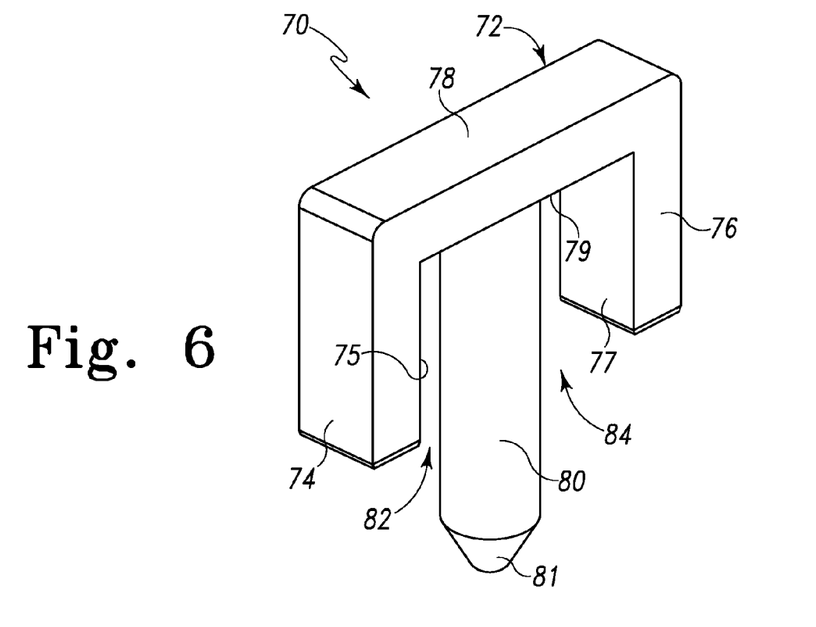
FIG. 6 is an enlarged isometric view of another embodiment of a spinal facet fastener fashioned in accordance with the principles of the present invention.
Figure 7:
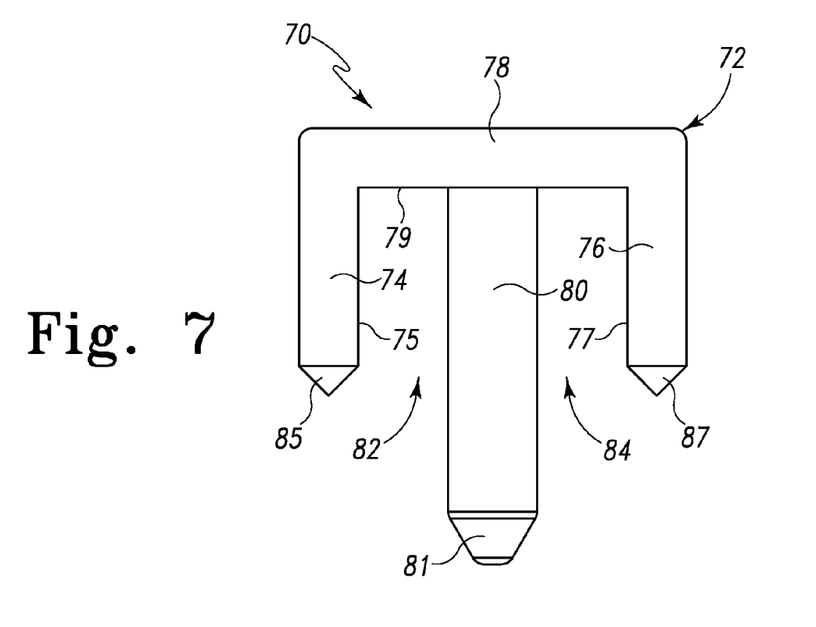
FIG. 7 is a side view of the spinal facet fastener of FIG. 6.

Referring to FIGS. 6 and 7, there is depicted an alternative embodiment of a spinal facet fastener fashioned as a spinal facet staple or tack, generally designated 70 (collectively, staple). The spinal facet staple 70 is characterized by a preferably, but not necessarily, unitary body 72. The body 72 has a first leg, member, post or the like 74 (collectively, leg 74), a second leg, member, post or the like 76 (collectively, leg 76) and a cross member 78 that all form a generally U-shaped body. It should be appreciated that the terms first and second are arbitrary unless indicated otherwise.

The first and second legs 74, 76 extend in the same direction from opposite ends of the cross-member 78. Preferably, but not necessarily, the first and second legs 74, 76 are at least generally parallel with one another, but may be skewed relative to one another if desired. The inner surfaces 75, 77 and 79 of the first and second legs 74, 76 and the cross member 78 of the spinal facet staple 70 are generally flat, smooth or planar.

The spinal facet staple 70 further includes a post, spike, nail or the like 80 having a conical tip 81 that extends from the underside 79 of the cross member 78 in like manner as the first and second legs 74, 76. The spike 80 is configured for reception in the spinal facet joint area between the inferior articular process of one vertebra and the superior articular process of another adjacent vertebra. The spike 80 is shown being longer in length than the first and second legs 74, 76. The first and second legs 74, 76 however, may be the same length if desired or longer. The body 72 thus defines two areas 82 and 84 on either side of the spike 80. Particularly, the area 82 is between the spike 80, the first leg 74 and a portion of the undersurface 79 of the cross member 78, while the area 84 is between the spike 80, the second leg 76 and a portion of the undersurface 79 of the cross member 78. While not shown, the spinal facet staple 70 may include serrations on the inner surfaces 75, 77 of first and second legs 74, 76 in like manner as the spinal facet clamp 30. Surface 80 may also be serrated to prevent backing out of the facet joint and to help tear the facet. This provides anti-kick-out and back-out provisions.

The view of the spinal facet staple 70 of FIG. 7 shows a spike 85 on the end of the first leg 74 and a spike 87 on the second leg 76. These allow the legs to wedge their way into the vertebral bone portions of the spinal facet joint. The view of FIG. 6 either does not show the spikes 85, 87 or is an alternate embodiment that does not have spikes.

Figure 8:
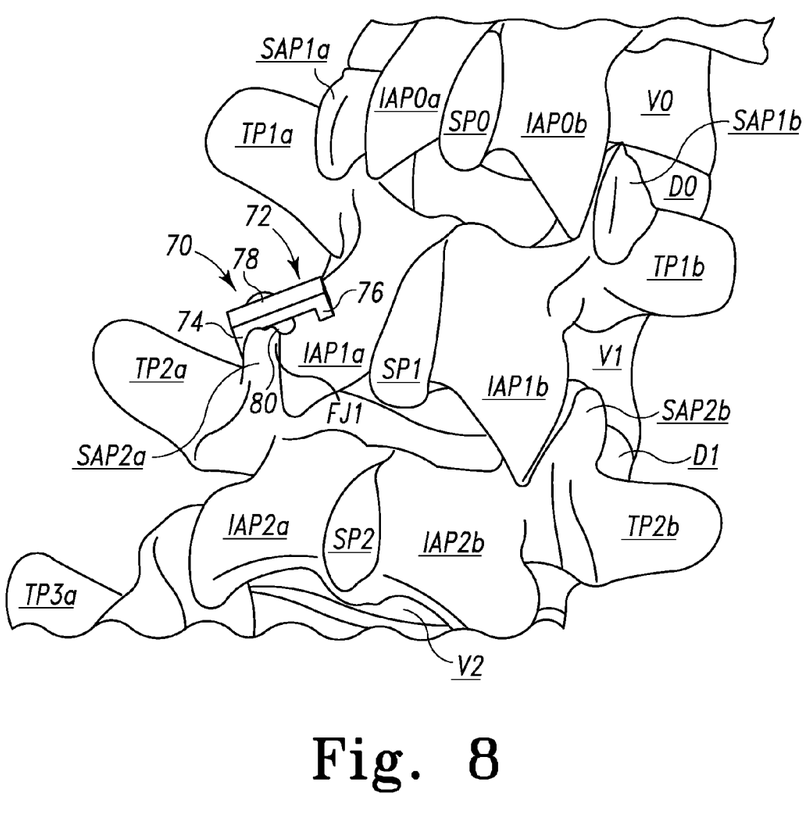
FIG. 8 is a posterior view of the portion of human spine as in FIG. 2 having the spinal facet fastener of FIGS. 6 and 7 situated thereon.

FIG. 8 shows spinal facet staple 70 is situated in the spinal facet joint FJ1 and particularly about one inferior articular process of a first vertebra V1 (labeled "IAP1a") of the spinal facet joint FJ1, and about one superior articular process of a second vertebra V2 (labeled "SAP2a") of the spinal facet joint FJ1). The spinal facet staple 70 holds, restrains and/or retains the spinal facet joint FJ1. The spinal facet staple 70 can thereby limit articulation of the spinal facet joint FJ1 or immobilize articulation of the spinal facet joint FJ1. Particularly, the spike 80 extends into the space between the inferior articular process (IAP1a) of the first vertebra V1 and the superior articular process (SAP2a) of the second vertebra V2. The first leg 74 extends into the bone of the superior articular process SAP2a while the second leg 76 extends into the bone of the inferior articular process IAP1a.

The portion of the spine shown in FIG. 8, like the portion of the spinal column or spine shown in FIGS. 2 and 3 represents any portion of the spine in which the present invention may be used such as the lumbar or thoracic portions. The nomenclature of FIG. 8 with respect to the vertebral parts is the same as that of FIGS. 2 and 3. The respective parts of these vertebrae are labeled with its respective number while transverse processes are labeled beginning with the letters "TP", the superior articular processes are labeled beginning with the letters "SAP", the inferior articular processes are labeled beginning with the letters "IAP", while the spinous processes are labeled beginning with the letters "SP."

Figure 9:
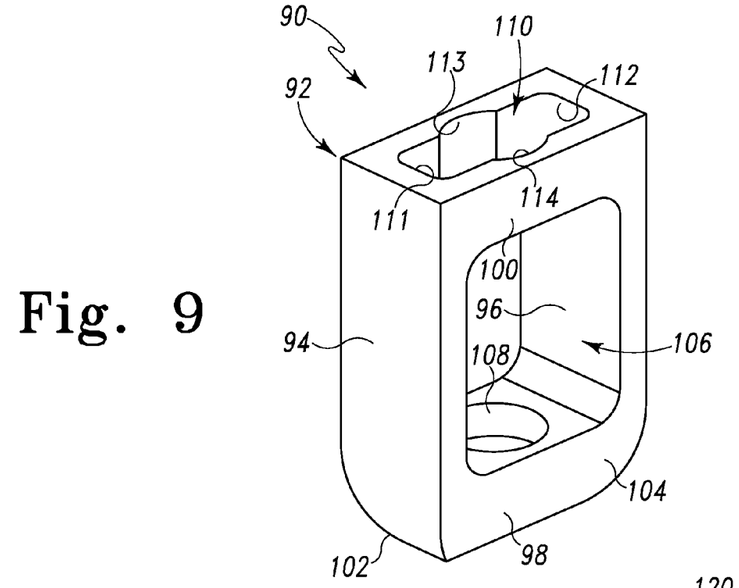
FIG. 9 is an enlarged isometric view of a spinal facet joint anchoring element that may be used with the spinal facet fastener of FIGS. 6 and 7.
Figure 11:
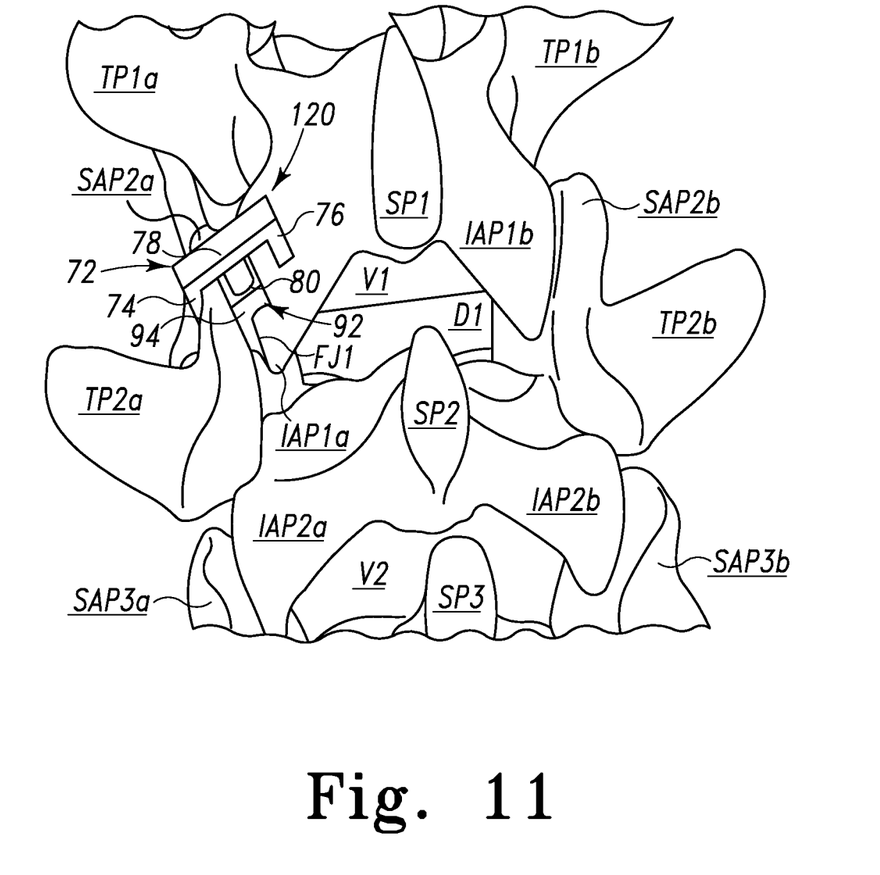
FIG. 11 is a posterior view of the portion of the human spine as in FIG. 8, but with the spinal facet fastener of FIG. 10 situated thereon.

FIG. 9 shows a spinal facet joint stabilizing or anchoring element/component generally designated 90 that may be used in conjunction with the spinal facet staple 70 of FIGS. 6 and 7. Particularly, as shown in FIG. 11, the anchoring element 90 is shown situated in the spinal facet joint FJ1 and particularly in the space between the inferior articular process of the first vertebra V1 (labeled "IAP1a") of the spinal facet joint FJ1, and the superior articular process of the second vertebra V2 (labeled "SAP2a") of the spinal facet joint FJ1. Again, the portion of the spine shown in FIG. 11, like the portion of the spinal column or spine shown in FIG. 8, represents any portion of the spine in which the present invention may be used such as the lumbar or thoracic portions. The nomenclature of FIG. 11 with respect to the vertebral parts is the same as that of FIGS. 2, 3 and 8. The respective parts of these vertebrae are labeled with its respective number while transverse processes are labeled beginning with the letters "TP", the superior articular processes are labeled beginning with the letters "SAP", the inferior articular processes are labeled beginning with the letters "IAP", while the spinous processes are labeled beginning with the letters "SP."

The anchoring component 90 is characterized by a preferably, but not necessarily, unitary body 92. The body 92 has a first side, leg, member or the like 94 (collectively, side 94), a second side, leg, member or the like 96 (collectively, side 96), a lower cross member 98 extending between lower ends of the first and second sides 94, 96, and an upper cross member 100 extending between upper ends of the first and second sides 94, 96 that all form a generally D-shaped body. As such, the first side 92 joins the lower cross member 98 at an angle while the second side 94 joins the lower cross member 98 at an arc. Moreover, the configuration defines an interior 106 bounded by the inner surfaces of the first and second sides 94, 96 and the upper and lower cross members 98, 100.

Figure 10:
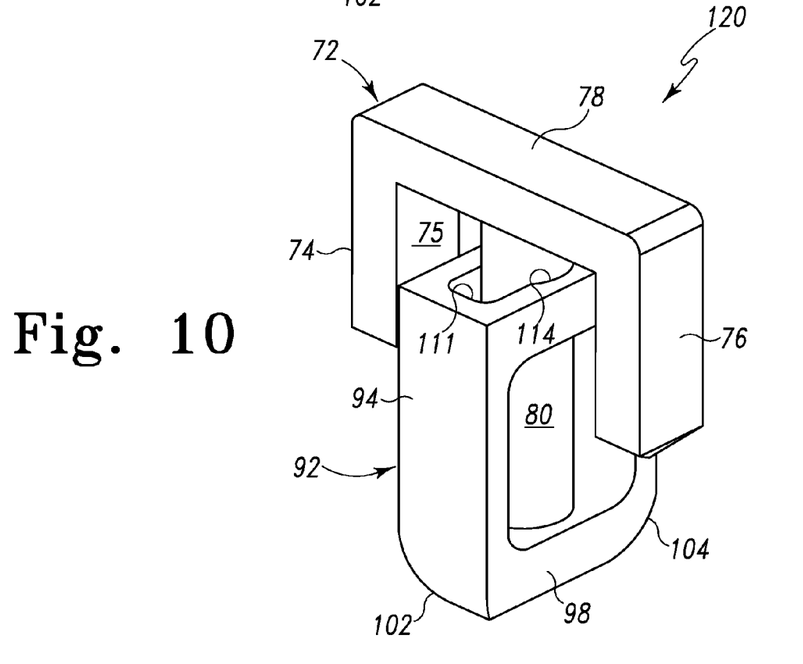
FIG. 10 is an enlarged isometric view of another embodiment of a spinal facet fastener utilizing the spinal facet joint anchoring element of FIG. 9 with the spinal facet fastener of FIGS. 6 and 7.

The upper cross member 100 has a configured bore 110 extending from the upper surface to the lower surface thereof. The configured bore 110 is generally rectangular and thus defines a first end 111 and a second end 112. First and second arc portions 113 and 114 are defined on either side of each other between the first and second ends 111, 112. The arc portions 113, 114 define a bore that is sized to receive the spike 80 of the spinal facet staple 70. The lower cross member 98 has a bore 108 that extends from an inner surface to an outer surface thereof. The bore 108 is sized to receive the spike 80. In this manner, the body 72 of the spinal facet staple 70 is pivotally received in the anchoring element 90 through receipt of the spike 80 in the bores 110, 108. This allows the rotational position of the legs 74, 76 relative to the anchoring element 90. Since the anchoring element 90 is received within the spinal facet joint, the legs 74, 76 of the facet staple 70 can be rotationally oriented for positional placement of the legs into the inferior and superior articular processes of the spinal facet joint. FIG. 10 depicts the spinal facet fastener 120 shown in FIG. 11 and described above which utilizes the anchoring element body 92 and the staple body 72.

Figure 12:
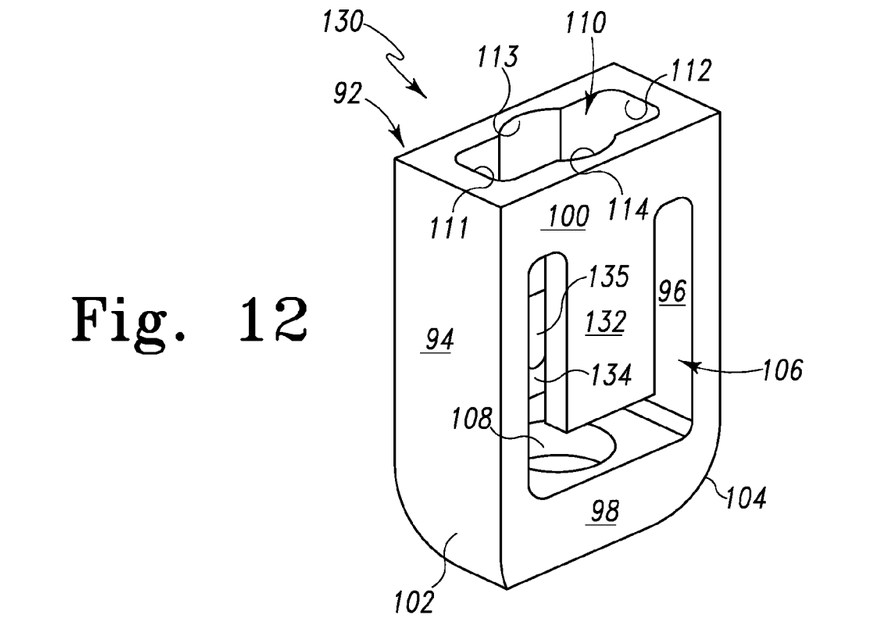
FIG. 12 is an enlarged isometric view of an alternate embodiment of the spinal facet joint anchoring element of FIG. 9.
Figure 13:
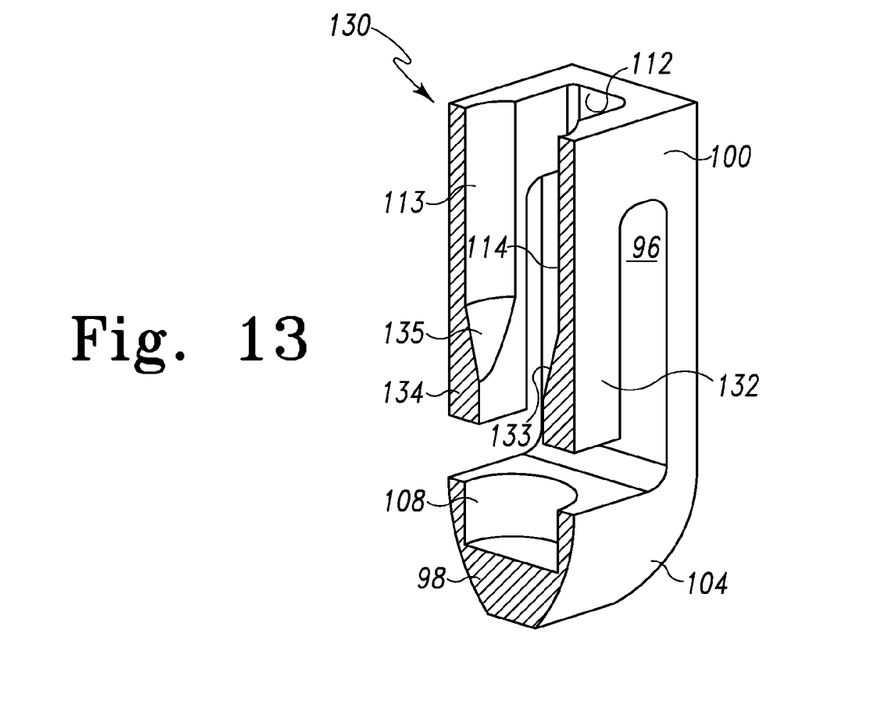
FIG. 13 is a sectional view of the anchoring element of FIG. 12.

FIGS. 12 and 13 show an alternate embodiment of the spinal facet joint stabilizing or anchoring element/component 90, now generally designated 130, that may be used in conjunction with the spinal facet staple 70 of FIGS. 6 and 7 in like manner to the anchoring element 90 of FIG. 9. The spinal facet joint anchoring element 130 is used in like manner to that shown in FIG. 11 with respect to the anchoring element 90. As such, the spinal facet joint anchoring element 130 is thus configured to be situated in the spinal facet joint FJ1 and particularly in the space between the inferior articular process IAP1a of the first vertebra V1 of the spinal facet joint FJ1, and the superior articular process SAP2a of the second vertebra V2 of the spinal facet joint FJ1.

The spinal facet joint anchoring element 130 has the same components as that of the spinal facet joint anchoring element 90. Therefore, the components of the present anchoring element are labeled the same as the spinal facet joint anchoring element 90. As such, the spinal facet joint anchoring element 130 has a preferably, but not necessarily, unitary body 92. The body 92 has a first side, leg, member or the like 94 (collectively, side 94), a second side, leg, member or the like 96

(collectively, side 96), a lower cross member 98 extending between lower ends of the first and second sides 94, 96, and an upper cross member 100 extending between upper ends of the first and second sides 94, 96 that all form a generally D-shaped body. As such, the first side 92 joins the lower cross member 98 at an angle while the second side 94 joins the lower cross member 98 at an arc. Moreover, the configuration defines an interior 106 bounded by the inner surfaces of the first and second sides 94, 96 and the upper and lower cross members 98, 100.

The upper cross member 100 has a configured bore 110 extending from the upper surface to the lower surface thereof. The configured bore 110 is generally rectangular and thus defines a first end 111 and a second end 112. First and second arc portions 113 and 114 are defined on either side of each other between the first and second ends 111, 112. The arc portions 113, 114 define a bore that is sized to receive the spike 80 of the spinal facet staple 70.

Additionally, a first elongated tab 132 extends from one side of the upper cross member 100 while a second elongated tab 134 extends from the other side of the upper cross member 100 opposite to the tab 132. As best seen in FIG. 13, the arc portion 114 of the bore 110 extends a distance down the inside surface of the tab 132, while the arc portion 113 of the bore 110 extends a distance down the inside surface of the tab 134. An inwardly angled portion 133 is provided at the end of the arc portion 114, while an inwardly angled portion 135 is provided at the end of the arc portion 113. The angled portions 133, 135 cause the respective tabs 132, 134 to push outward upon receipt of the shaft 80 of the spinal facet tack so as to provide a wedging effect.

The lower cross member 98 of the anchoring element 130 has a bore 108 that extends from an inner surface to an outer surface thereof. The bore 108 is sized to receive the shaft of the spinal facet joint tack. The body of the spinal facet joint tack is pivotally received in the anchoring element 130 through receipt of the shaft in the bores 110, 108. This allows the rotational position of the legs of the spinal facet joint tack relative to the anchoring element 130. Since the anchoring element 130 is wedged within the spinal facet joint through expansion of the tabs 132, 134, the legs of the facet tack can be rotationally oriented for positional placement of the legs into the inferior and superior articular processes of the spinal facet joint.

While the invention has been illustrated and described in detail in the drawings and foregoing description, the same is to be considered as illustrative and not restrictive in character, it being understood that only preferred embodiments have been shown and described and that all changes and/or modifications that come within the spirit of the invention are desired to be protected.

What is claimed is:

1. A spinal implant comprising:
an anchoring element configured to be received within a spinal facet joint and comprising:
first and second end sides;
first and second upper cross-members extending laterally between the first and second sides; and
first and second tabs extending from the first and second upper cross members, respectively, the first and second tabs configured to engage opposing surfaces of a spinal facet joint;
wherein the first upper cross member and the first tab form a generally smooth first elongated arc portion, and wherein the second upper cross member and the second tab form a generally smooth second elongated arc portion facing the first elongated arc portion; and a spinal fastener comprising:
a first leg configured to abut a surface of an inferior articular process of a first vertebra that forms one portion of a spinal facet joint between the first vertebra and an adjacent second vertebra;
a second leg configured to abut a surface of a superior articular process of the adjacent second vertebrae that forms another portion of the spinal facet joint between the first vertebra and the adjacent second vertebra;
a fastener cross-member coupling the first and second legs and maintaining the first and second legs in a spaced-apart relationship; and
a post configured to be inserted at least partially within the anchoring element and slidably received by the first and second elongated arc portions, wherein insertion of the post into the anchoring element causes a deflection of the first and second tabs outward relative to lateral sides of the anchoring element to a deflected position wherein the post is rotatable relative to the anchoring element when the first and second tabs are in the deflected position;
the spinal implant restricting flexion and/or extension of the spinal facet joint when received about the spinal facet joint.

2. The spinal implant of claim 1, wherein:
the first leg has a smooth inner surface that abuts the surface of the inferior articular process of the first vertebra; and
the second leg has a smooth inner surface that abuts the surface of the superior articular process of the adjacent second vertebra.

3. The spinal implant of claim 1, wherein:
the first leg has a serrated surface that abuts the surface of the inferior articular process of the first vertebra; and
the second leg has a serrated inner surface that abuts the surface of the superior articular process of the adjacent second vertebra.

4. The spinal implant of claim 1, wherein the first leg, the second leg, and the cross-member are all composed of PEEK.

5. The spinal implant of claim 4, wherein the first and second legs and the cross-member form a U.

6. A spinal implant comprising:
a first leg configured for reception in a first vertebral bone of a spinal facet joint;
a second leg configured for reception in a second vertebral bone of the spinal facet joint;
a cross-member connected to and between the first and second legs such that the first and second legs each comprises a first end coupled to the cross-member and a second end extending away from the cross-member in a first direction; and
a spike provided on the second end of each of the first and second legs and extending in the first direction to facilitate reception of the first and second legs in the first and second vertebral bones of the spinal facet joint;
a post extending from the cross-member and between the first and second legs, the post comprising a conical tip extending from a generally smooth cylindrical portion;
an anchoring element configured to receive the post, the anchoring element including:
first and second upper cross members extending between first and second sides; and
first and second tabs extending from the first and second upper cross members, respectively;
wherein the first upper cross member and the first tab form a generally smooth first elongated arc portion, and wherein the second upper cross member and the second tab form a generally smooth second elongated arc portion facing the first elongated arc portion, wherein the post is slidably received by the first and second elongated arc portions such that the first and second tabs are deflected outward;

the spinal implant restricting flexion and/or extension of the spinal facet joint when received about the spinal facet joint.

7. The spinal implant of claim 6, wherein the first leg, the second leg, and the cross-member are all composed of PEEK.

8. The spinal implant of claim 7, wherein the first and second legs and the cross-member form a U.

9. The spinal implant of claim 6, wherein the anchoring element is composed of PEEK.

10. The spinal implant of claim 6, wherein the anchoring element forms a hollow frame.

11. A spinal facet implant comprising:
   an anchoring element, the anchoring element comprising first and second side members and first and second upper cross members extending between the first and second side members, and further comprising generally D-shaped first and second lateral surfaces, wherein first and second tabs extend from the first and second upper cross members, respectively to form co-facing first and second elongated arc portions;
   a fastener comprising:
      a first segment configured to be received in bone of an inferior articular process of a first vertebra forming one portion of a spinal facet joint between the first vertebra and an adjacent second vertebra;
      a second segment configured to be received in bone of a superior articular process of the adjacent second vertebrae forming another portion of the spinal facet joint between the first vertebra and the adjacent second vertebra;
      a cross-member connected between the first and second segments and maintaining the first and second segments in a spaced-apart relationship such that the first and second segments each comprises a first end coupled to the cross-member and a second end extending away from the cross-member in a first direction; and
      a spike provided on the second end of each of the first and second segments and extending in the first direction;
      a post extending from the cross-member between the first and second segments and configured to be slidably received by the first and second elongated arc portions of the anchoring element to expand the tabs in opposite outward directions;
   the spinal implant restricting flexion and/or extension of the spinal facet joint when installed.

12. The spinal facet implant of claim 11, wherein the first segment, the second segment, and the cross-member are all composed of PEEK.

13. The spinal facet implant of claim 11, wherein the anchoring element is composed of PEEK.

14. The spinal facet implant of claim 11, wherein the anchoring element forms a hollow frame.

15. The spinal facet implant of claim 14, wherein the anchoring element includes the first and second tabs that retain the post; wherein insertion of the post into the anchoring element causes outward deflection of the first and second tabs relative to the post, and wherein the post is rotatable relative to the anchoring element after deflection of the first and second tabs.

16. The spinal facet implant of claim 11, wherein the, the first and second elongated arc portions configured to generally conform to the periphery of the post.

* * * * *